United States Patent [19]

Pulverer et al.

[11] Patent Number: 4,946,830

[45] Date of Patent: Aug. 7, 1990

[54] AGENT AND METHOD FOR THE PREVENTION OF METASTASES OF MALIGNANT TUMORS

[76] Inventors: Gerhard Pulverer, Mohnweg 25, 5000 Cologne 40; Kurt Oette, Braunstrasse 39; Gerd Uhlenbruck, Gleueler Strasse 308, both of 5000 Cologne 41, all of Fed. Rep. of Germany

[21] Appl. No.: 44,483

[22] Filed: May 1, 1987

[30] Foreign Application Priority Data

May 9, 1986 [DE] Fed. Rep. of Germany ....... 3615621

[51] Int. Cl.$^5$ .................. A01N 43/04; C07G 3/00; C07G 00/00; C07H 5/04
[52] U.S. Cl. .......................... 514/23; 514/53; 514/62; 536/4.1; 536/18.7; 536/53.0
[58] Field of Search ............... 514/23, 53, 62; 536/4.1, 53.0, 18.7

[56] References Cited

U.S. PATENT DOCUMENTS

| | | | |
|---|---|---|---|
| 3,931,402 | 1/1976 | Ghielmetti et al. | 514/23 |
| 4,243,663 | 1/1981 | Azuma et al. | 514/23 |
| 4,316,983 | 2/1982 | Bllag | 536/53.0 |
| 4,334,017 | 6/1982 | Plotkin et al. | 435/7 |
| 4,389,392 | 6/1983 | Adachi | 436/64 |
| 4,455,380 | 6/1984 | Adachi | 436/63 |
| 4,496,539 | 1/1985 | Plotkin | 424/94.4 |
| 4,656,159 | 4/1987 | McPherson et al. | 514/23 |
| 4,742,046 | 5/1988 | Bollig | 514/8 |

OTHER PUBLICATIONS

Beuth et al., *Cancer Research and Clin. Onocology* (1987) 113:51–55.
Uhlenbruck et al., *Experientia* 43(1987), Birkhäuser Verlog, CH-4010 Basel/Switzerland.
Schirrmacher et al., *Clin. Expl. Metastases*, 1988, vol. 6, No. 2, 115–120.
Rozkowski et al., *Experientia* (in press), "Blocking of Lectin-Like Adhesion Molecules on Pulmonary Cells Inhibits Lung Sarcoma L-1 Col. in BALB/c-mice".
Pulverer et al. *J. Cancer Res Clin. Onocol.*, (1988) 114:217-220.
Roszkowski et al. *Experientia*, 45 (1989) pp. 584–588.

*Primary Examiner*—Ronald W. Griffin
*Assistant Examiner*—Pamela S. Webber
*Attorney, Agent, or Firm*—Wegner & Bretschneider

[57] ABSTRACT

Agents and methods for the prevention of metastases of malignant tumors use the monosaccharides which are specific for organ cell lectins and/or glycoconjugates containing these monosaccharides, and more specifically, β-D-galactose and/or glycoconjugates containing terminal β-D-galactose moieties.

4 Claims, No Drawings

AGENT AND METHOD FOR THE PREVENTION OF METASTASES OF MALIGNANT TUMORS

The formation of metastases of malignant tumors, initiated from a primary tumor at more or less remote locations of the body, is one of the most serious problems of tumor therapy, since most of the fatal conditions are caused by such metastases. In recent years there has been considerable success in the treatment of primary tumors by surgery, radiation therapy and chemotherapy. In contrast thereto, the treatment of metastases is extremely difficult and only rarely successful. The risk of metastasis formation is particularly high during the treatment of primary tumors so that there is an urgent need for preventing the formation of metastases especially in this phase. Thorough investigations of metastasis formation, that is of organ-specific and non-organ-specific metastases, have resulted in the finding that organ cell lectins are responsible for the formation of metastases. Lectins are highly specific sugar-binding molecules which were first found only in plants, but later on in nearly all other living creatures including vertebrates. The lectins apparently mainly serve to recognize sugar structures on cell surfaces or in soluble glycoconjugates. It was further found that organ cell lectins are responsible for the specific organotropic metastasization. In the course of further intensive investigations it was now found that the formation of metastases of malignant tumors can even be prevented by saturating these organ cell lectins with the monosaccharides specific therefor and/or with glycoconjugates containing said monosaccharides in terminal positions. For this purpose, $\beta$-D-galactose and/or glycoconjugates containing terminal $\beta$-D-galactose appear to be of particular importance. Further important monosaccharides are mannose and glycoconjugates containing terminally or centrally located mannose as well as L-fucose, N-acetylglucosamine, N-acetylgalactosamine, N-acylneuraminic acids and derivatives containing neuraminic acid. Thus, the glycoconjugates are substances which have the specific monosaccharide bonded in a terminal or central position to a pharmacologically inert carrier molecule. This carrier molecule itself should not be cytotoxically active against tumor cells. Thus, typical carrier molecules in the simplest cases are other sugars, so that, for the purposes of the invention, in addition to the specific monosaccharides themselves, disaccharides, trisaccharides and oligosaccharides containing them can be employed. It is preferred that the glycoconjugates are not or are only weakly immunogenic so that they do not cause side effects or are deactivated by the immune response.

In the glycoconjugates containing the specific monosaccharides the latter should preferably be bonded in the terminal positions. However, it has been shown that centrally bonded monosaccharides are also active. In this latter case it has, however, not yet been elucidated whether in these glycoconjugates one or another moiety is so readily removed that glycoconjugates having a terminal specific monosaccharide moiety are rapidly formed in vivo.

It has now been shown that, for example, colon carcinoma tends to form metastases in the liver. It has further been shown that metastasis can be completely prevented by administration of galactose or glycoconjugates containing galactose such as arabino-galactan. By comparative tests using mannan as a galactose-free control substance it could be shown that the same metastasization behavior as in an untreated control group remains. The application of galactose or arabinogalactan is only necessary for a relatively short period before and after the treatment of the primary tumor or shortly before and after diagnostic interventions that might potentially result in metastasization in cases of suspicion of a tumor. However, if no side-effects are to be feared, then the monosaccharides and/or glycoconjugates containing these monosaccharides may be administered from the time of the diagnosis of the tumor until some weeks after the therapy. The treatment with monosaccharides specific for organ cell lectins and/or glycoconjugates containing these monosaccharides is of course only efficient with respect to a prevention of an organ-specific colonization of metastases. However, this organ-specific metastasization appears to occur particulary frequently and, thus, to be particularly dangerous. Thus, to be able to suppress organ-specific metastasis is already an important therapeutic success.

Accordingly, it is one object of the present invention to provide agents for the prevention of metastases of malignant tumors in mammals, which agents contain the monosaccharides which are specific for organ cell lectins and/or glycoconjugates containing these monosaccharides. More specifically, said agents are those containing $\beta$-D-galactose and/or glycoconjugates containing terminal $\beta$-D-galactose moieties.

Another object of the invention is the method of using monosaccharides which are specific for organ cell lectins and/or glycoconjugates containing these monosaccharides for the prevention of metastases of malignant tumors in mammals. A further object of the invention is the use of monosaccharides which are specific for organ cell lectins and/or glycoconjugates containing these monosaccharides for the preparation of agents for the prevention of metastases of malignant tumors.

In particular, in the cases where the tumors tend to form organ-specific metastases, it can now be selectively examined whether the organ cell lectins responsible therefor can be blocked by an application of the corresponding monosaccharide and/or glycoconjugates containing these monosaccharides.

Since galactose and glycoconjugates containing galactose are well compatible, the new therapy can be carried out in a relatively simple manner and without problems. Said active substances may be applied by the enteral as well as parenteral routes. They are metabolized or excreted from the organism in known manner. The relatively high serum level of galactose obviously is absolutely sufficient to block the crucial organ cell lectins as long as there is a danger of an increased metastasization due to treatment of the primary tumor. The same is true, of course, to the phase of diagnostic surgical interventions during which tumor cells may readily get into the blood circulation. The test results indicate that the monoclonal antibodies against the organ cell lectins stop the metastasization in a similar manner as the specific monosaccharides now found to be highly active and/or the glycoconjugates containing these monosaccharides, preferably in the terminal position. It is obvious that the agents of the invention can be handled in a simpler way, at lower cost, and more safely than the monoclonal antibodies which are difficult and expensive to prepare.

Extensive animal experiments were followed by successful clinical investigations which showed, for example, that upon administration to patients of 120 to 150 g of galactose per day in cases of a diagnosed colon carcinoma from the time of diagnosis until 4 weeks after the successful therapy, no liver metastases were observed, although these metastases are statistically very frequently observed without the application of galactose. The amounts of galactose used are tolerated over an extended period without occurrence of side effects. Animal experiments showed that arabinogalactan is also active. Neuramine-specific organ lectins could be successfully blocked by using bacteria preparations from Streptococci and Propionibacteria treated with neuraminidase. As the arabinogalactan there was employed a preparation from Larix europaea having an average molecular weight of 70,000 (Serva GmbH, Heidelberg, West Germany). It is a non-immunogenic oligosaccharide which may also be used as a plasma expander.

Animal experiments employing galactan from gum arabic, dextran and mannan and other mono- and disaccharides showed that these are not capable of blocking the galactose-specific lectins of the liver and, thus, to suppress a metastasis colonization in the liver.

EXAMPLE 1—MATERIALS AND METHODS

The in vivo studies were carried out in Balb/c mice, 8–12 weeks old, weighing 20–22 g. The animals were kept in plastic cages and allowed free access of food and water.

For the in vivo experiments, sarcoma L-1 tumor (Institute of Oncology, Warsaw, Poland) was used. This tumor arose spontaneously in the lung of a Balb/c mouse and was maintained in this species of mice. Implanting of sarcoma L-1 cells subcutaneously into the limbs of the animals induced growth of a local, solid tumor and multiple (40–100, nonconfluent, well countable) lung metastases. Lung tumor nodules were present 14 days after tumor cells were inoculated intravenously. The primary tumors were dissected from donor mice, minced with scissors and rubbed through a steel sieve. Approximately 80–85 serial passages of the tumor were made. The cells were washed, suspended in RPMI 1640 (Gibco Grand Island, N.Y.), and $1 \times 10^5$ viable tumor cells in 0.1 ml phosphate-buffered saline (PBS) were injected subcutaneously for the serial passages of the tumor. Injections into the tail vein of mice were used for the lung and liver colony assays. Viability was tested with trypan blue dye exclusion. Lung or liver tumor nodules were counted 14 days after sarcoma cell inoculation. Tumor nodules were regarded as uncountable when more than 150 or confluent nodules were found.

Arabinogalactan from Larix Europaea with an average molecular weight of about 70,000 daltons was obtained from Serva GmbH, D-6900 Heidelberg, Federal Republic of Germany. Alpha$_1$-acid-(asialo)glycoprotein was obtained from Behringwerke AG, Marburg, Germany and tritiated according to the method of Pricer and Ashwell, J. Biol. Chem. 246: 4825 (1971).

Arabinogalactan was injected intraperitoneally at a dosage of 0.5 mg/g body weight (solubilized in 0.2 ml PBS). D-galactose was injected at a dosage of 1 or 2 mg/g body weight; given i.p., it is rapidly metabolized and eliminated.

For neuraminidase treatment, 1 ml of the sarcoma cell-RPMI suspension ($10^6$ to $10^7$ viable cells per ml) was incubated with 1 unit Vibrio cholerae neuraminidase for one hour at 37° C. The reaction was terminated by washing the cells 3 times in PBS.

EXAMPLE 2—LIVER LECTIN (HBP) BLOCKING ACTIVITY IN BALB/C MICE

The liver lectin (HBP) blocking activity of D-galactose and arabinogalactan was tested by intravenous administration of tritiated alpha$_1$-acid (asialo)glycoprotein to Balb/c mice (100 mg solubilized in 0.1 ml PBS). This glycoprotein showed rapid clearance within 15 minutes from the circulation and uptake by the liver. Preinjection of arabinogalactan (15 min. before glycoprotein injection) caused a markedly delayed elimination of the asialo-glycoprotein from the serum. After 120 minutes, the radioactivity in the serum was still measurable. Three experiments (spreading less than 5%) manifested 123 dpm/microliter serum after alpha$_1$-acid(asialo)-glycoprotein injection without receptor blocking compared to 224 dpm/microliter serum after receptor blocking by preinjection with arabinogalactan. The same was true for for D-galactose, although its rapid metabolism and elimination led to a shorter receptor blockage. After 30 minutes, an increase in radioactivity of more than 90% was present in serum (105 dpm/micro liter serum after alpha$_1$-acid-(asialo)glycoprotein injection without receptor blocking compared to 200 dpm/microliter after receptor blocking by preinjection with D-galactose). Blockage was decreased by approximately 50% after 60 minutes incubation. Thus, liver lectin (HBP) was blocked by application of D-galactose and by the galactose-containing glycoconjugate (arabinogalactan).

EXAMPLE 3—INHIBITION OF LIVER COLONIZATION BY ADMINISTRATION OF D-GALACTOSE AND ARABINOGALACTAN

In order to prove the hypothesis that the settling of a malignant tumor into the liver is associated with a recognition process, involving a D-galactose-specific lectin-carbohydrate interaction, which can be inhibited by competitive glycoconjugates, colonies of mouse sarcoma L-1 tumor cells in Balb/c mice were investigated. The receptor blocking activity was investigated using several glycoconjugates with various concentrations of D-galactose and with mannan, a galactose-free control polysaccharide. Preinjection (one hour before intravenous implantation of neuraminidase-treated tumor cells) and regular i.p. injections (days 1–3, 12 hour intervals; days 4–10, 24 hour intervals) of arabinogalactan completely prevented the settling of tumor cells in the liver. However, this treatment did not influence the homing to the lung. The number and average diameter of the tumor nodules in the lung did not differ from the control group. Mannan, a control polysaccharide without galactose, did not alter the pattern of colonization to lung and liver or the number of tumor nodules in those organs. All other galactans (and other substances, e.g., galactan from gum arabic, gum arabic from the acacia tree, dextran 40, dextran 70, and PBS) also failed to inhibit metastases to the liver or decrease the number of tumor nodules in lung and liver.

EXAMPLE 4—ESTABLISHMENT OF OPTIMUM TIMING SCHEDULE OF D-GALACTOSE REGIMEN

The most favorable dose and timing for inhibition of liver metastasis by treatment D-galactose was determined. I.p. inoculation of 1 or 2 mg/g body weight of D-galactose (one hour before tumor cell inoculation and for 3 days at 8 hour intervals) was most effective reduction of metastases in the liver. When sarcoma cells were inoculated 3 days after the last i.p. inoculation of D-galactose, no inhibitory effect on liver metastasis was observed. These results confirmed the hypothesis that D-galactose temporarily blocked liver lectins (HBP). These receptors were unoccupied and accessible again when sarcoma cells were inoculated 3 days after the last inoculation of D-galactose.

CLINICAL DOSAGE: Administration to patients starts preferably 8–12 hours before operation or diagnostic intervention and is usually continued 3 days post-operatively, although longer administration can be practiced in the absence of side effects.

D-galactose is administered so as to supply a total dosage of 1–3 mg/kg body weight in 24 hours by infusion every 8 hours.

Arabinogalactan is given in a total daily dosage of about 0.1–1 mg/kg body weight, preferably 0.5 mg/kg body weight by infusion, administration being distributed over the whole 24 hour period.

We claim:

1. Method for preventing metastases of malignant tumors in a mammal which comprises the administration of an effective amount of a monosaccharide which is specific for organ cell lectins, wherein the monosaccharide is selected from the group consisting of beta-D-galactose, glycoconjugates of beta-D-galactose, mannose, glycoconjugates of mannose, L-fucose, N-acetylglucosamine, N-acetylgalactosamine and N-acylneuraminic acid.

2. Method of claim 1, wherein the monosaccharide administration is β-D-galactose.

3. Method of claim 1, wherein the compound administered is a β-D-galactose glycoconjugate.

4. Method of claim 1, wherein the malignant tumors are color or liver tumors.

* * * * *